US007957568B2

(12) United States Patent (10) Patent No.: US 7,957,568 B2
Adachi et al. (45) Date of Patent: Jun. 7, 2011

(54) IMAGE INTERPRETATION REPORT CREATING APPARATUS AND IMAGE INTERPRETATION SUPPORT SYSTEM

(75) Inventors: Yuuma Adachi, Minato-ku (JP); Shouji Kanada, Minato-ku (JP); Takahiro Ito, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 918 days.

(21) Appl. No.: 11/511,376

(22) Filed: Aug. 29, 2006

(65) Prior Publication Data

US 2007/0053567 A1 Mar. 8, 2007

(30) Foreign Application Priority Data

Aug. 31, 2005 (JP) .................................. 2005-251575

(51) Int. Cl.
*G06K 9/00* (2006.01)
(52) U.S. Cl. ..................................................... 382/128
(58) Field of Classification Search .................... 382/128
See application file for complete search history.

(56) References Cited

U.S. PATENT DOCUMENTS

| 6,901,277 | B2 * | 5/2005 | Kaufman et al. | ............. | 600/407 |
| 2003/0016850 | A1 * | 1/2003 | Kaufman et al. | ............. | 382/128 |
| 2005/0085709 | A1 * | 4/2005 | Pelletier et al. | ............... | 600/410 |
| 2005/0177394 | A1 * | 8/2005 | Hosoya et al. | .................... | 705/2 |

FOREIGN PATENT DOCUMENTS

| JP | 4314436 A | 11/1992 |
| JP | 581353 A | 4/1993 |
| JP | 11-250263 A | 9/1999 |
| JP | 2000339341 A | 12/2000 |
| JP | 2001120541 A | 5/2001 |
| JP | 2001137230 A | 5/2001 |
| JP | 2002-253545 A | 9/2002 |
| JP | 2002-342485 A | 11/2002 |
| JP | 2005027978 A | 2/2005 |

OTHER PUBLICATIONS

Japanese Office Action corresponding to Japanese Patent Application No. 2005-251575, dated Nov. 4, 2010.
Kiyoshi Shibuya, et al., Temporal Change of Precancerous Lesion, "Way of Medicine", vol. 199, No. 9, Dec. 1, 2001, Ishiyaku Publishers, Inc., pp. 593-596.
Japanese Office Action corresponding to Japanese Patent Application No. 2005-251575, dated Jul. 17, 2010.

* cited by examiner

*Primary Examiner* — Hadi Akhavannik
(74) *Attorney, Agent, or Firm* — Sughrue Mion, PLLC

(57) ABSTRACT

An image interpretation report creating apparatus for retrieving a key image corresponding to that in the previous examination from among images taken in this examination to display it on an image display terminal. The apparatus includes: a follow-up observation examination determining unit for determining whether this examination is an object of follow-up observation; a previous report determining unit for determining, as previous report data, report data on the same patient from among the report data; a previous report data acquiring unit for acquiring the previous report data; an image data acquiring unit for acquiring image data at this time; a key image estimating unit for estimating a key image at a slice position corresponding to the previous examination based on the previous report data; and an image data output unit for outputting image data representing examination images containing the key image to the image display terminal.

19 Claims, 9 Drawing Sheets

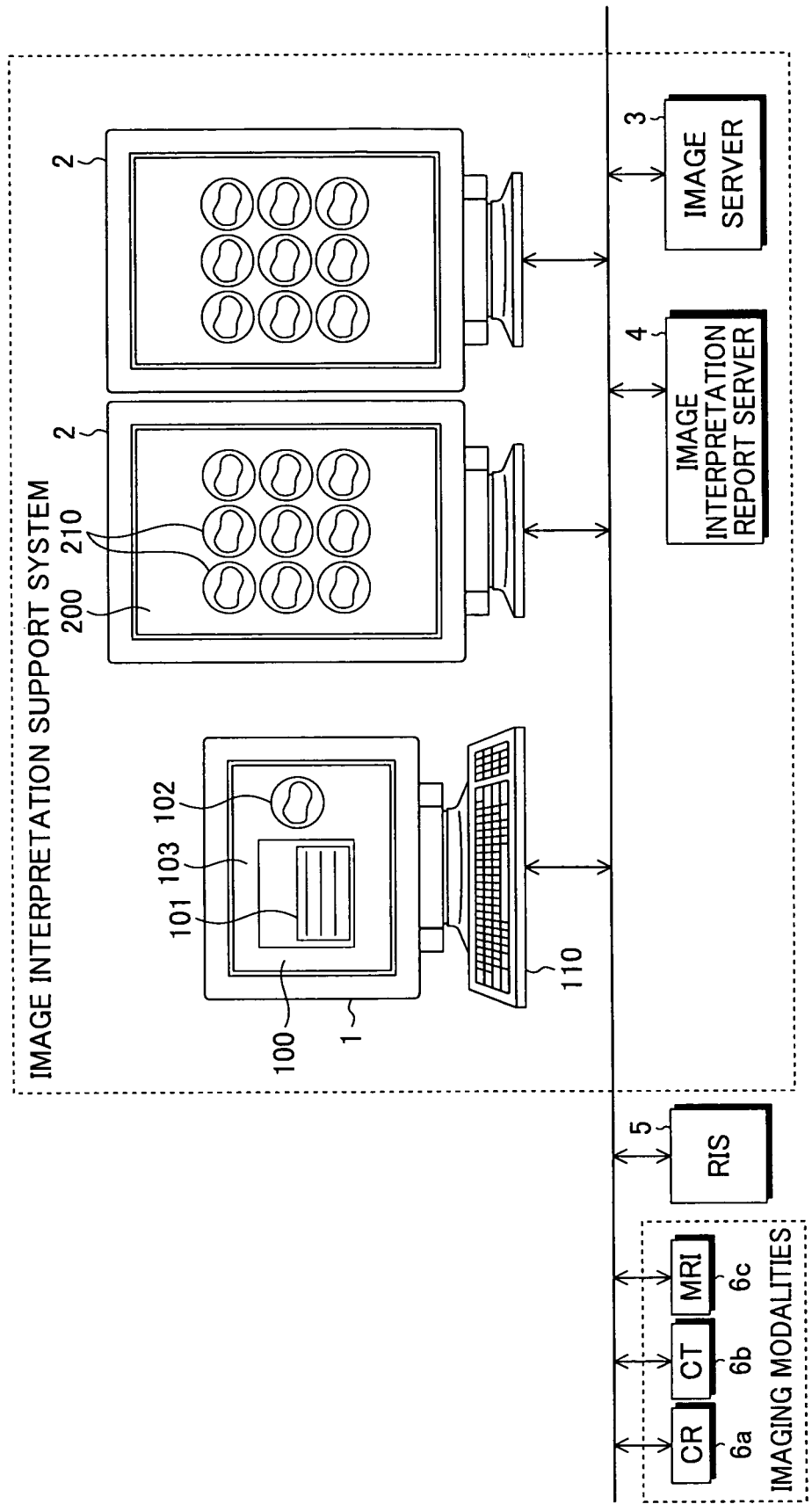

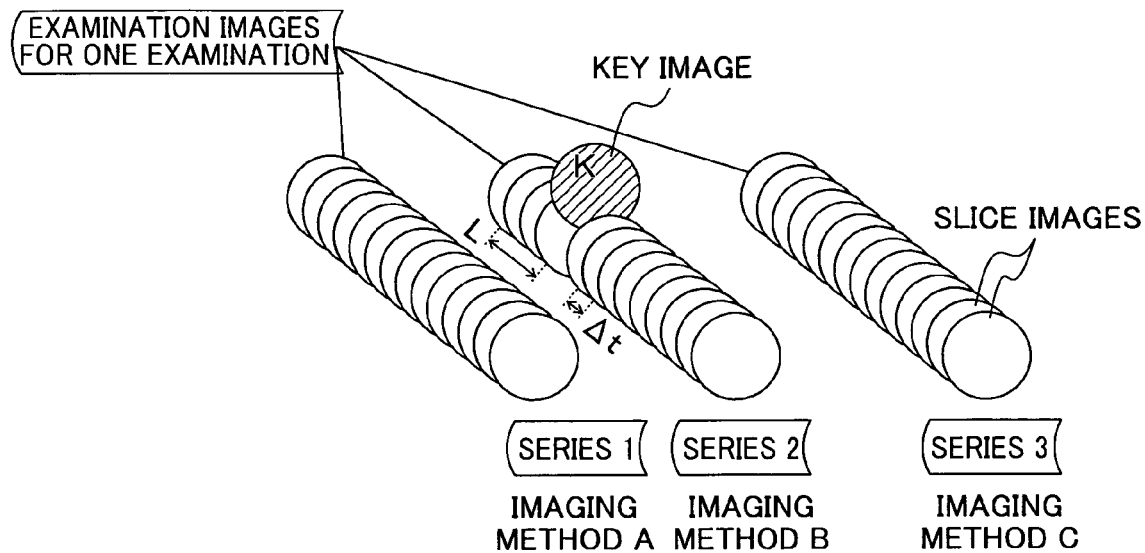

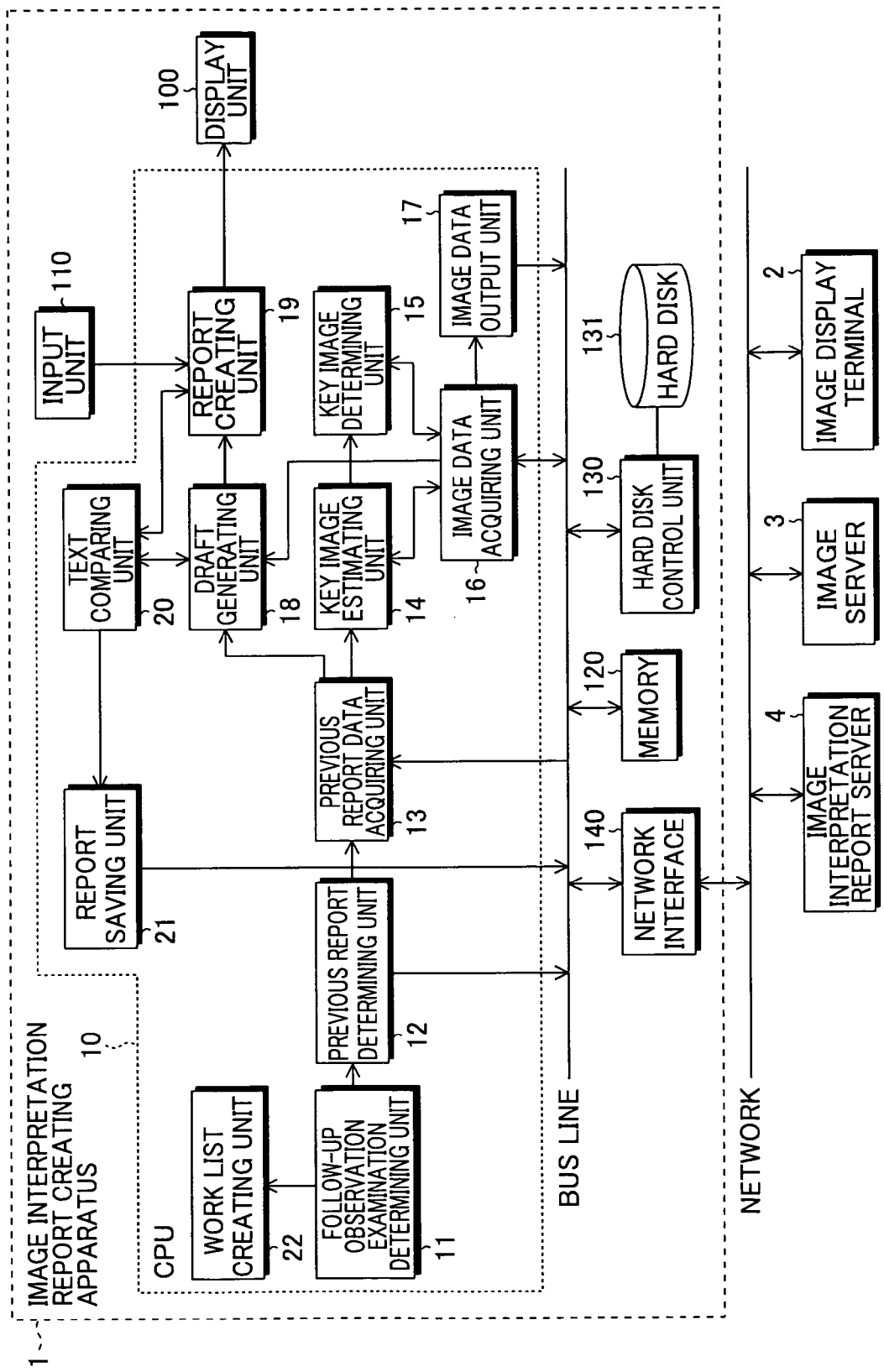

FIG.6
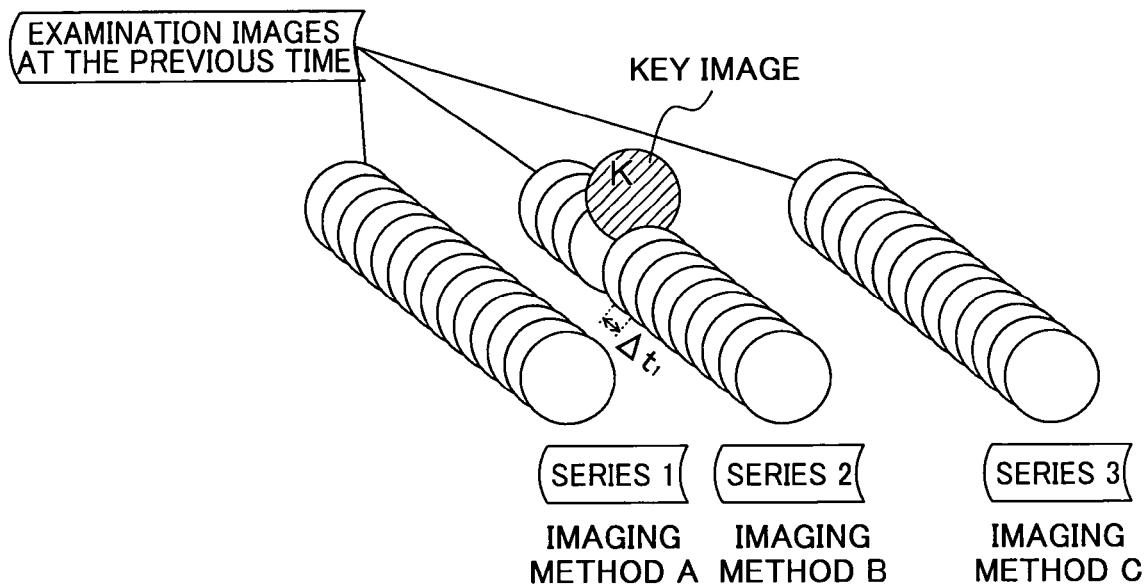
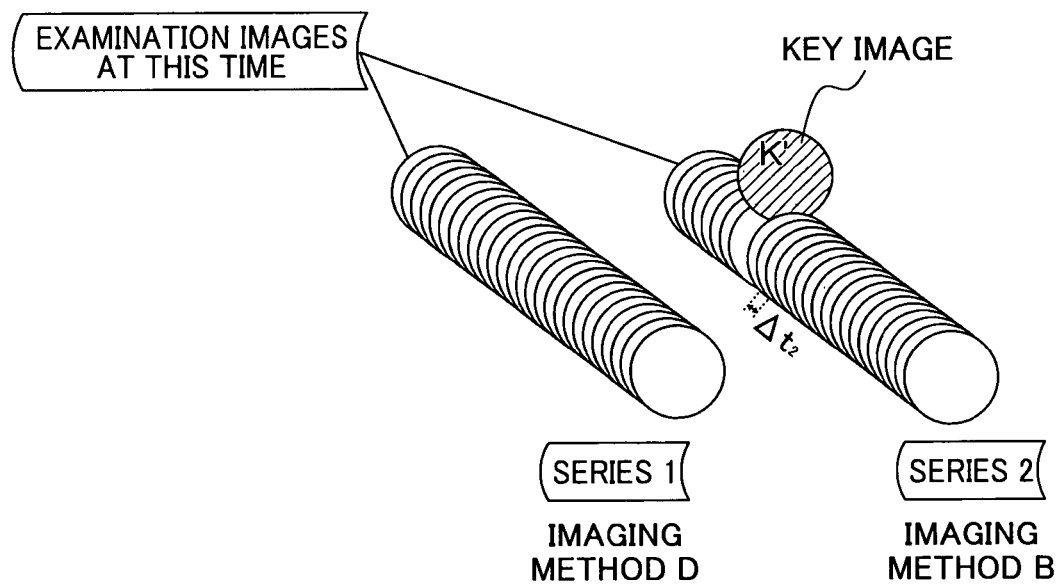

IMAGE INTERPRETATION REPORT CREATING APPARATUS AND IMAGE INTERPRETATION SUPPORT SYSTEM

BACKGROUND OF THE INVENTION

1. Field of the Invention

The present invention relates to an image interpretation report creating apparatus to be used for creating image interpretation reports and an image interpretation support system for supporting image interpretation performed by doctors after imaging of examination images (medical images) used for medical diagnoses.

2. Description of a Related Art

Recent years, along with the spread of medical digital image generation technologies such as CR (computed radiography), MRI (magnetic resonance imaging) and CT (computed tomography), medical images obtained by examinations have been electronically managed.

Generally, when an imaging examination is performed, interpretation is performed on generated images by an image interpretation doctor to create an image interpretation report, in which an interpretation result and observations are written, before a specific diagnosis is made to a patient by a doctor in charge. Conventionally, even when digital image data is generated, medical images printed on photographic films are used at the time of image interpretation. On the other hand, medical images displayed on monitors are also used for image interpretation with the development of high-definition monitors (viewers).

By the way, when a follow-up observation of a lesion part is performed, it is necessary for the image interpretation doctor to observe images representing the same part as that in the past examination. Accordingly, it is desirable that whether or not the same examination as this examination has been made can be determined on the stored past examination images, or that the past examination images can be easily searched.

As a related technology, Japanese Patent Application Publication JP-P2002-342485A discloses an image interpretation support system in which image interpretation reports are created or referred by using an image interpretation report terminal while medical images are displayed on an image display terminal. The image interpretation support system includes means for determining report information that matches a predetermined condition from an image interpretation report database at regular time intervals or according to a user's instructions, means for determining image information corresponding to the report information of the determination result from an image database, means for merging report information and image information with respect to each examination to make and display a list of examinations on which the image information has been obtained, means to be used by the user for selecting one examination from the displayed list of the examinations and giving instructions to display the examination, means for transmitting report display instructions to an image interpretation report terminal in accordance with image interpretation report identification of the selected examination, means for displaying an image interpretation report corresponding to the image interpretation report identification in the image interpretation report terminal that has received the report display instructions, means for transmitting image display instructions to an image display terminal in accordance with image identification of the selected examination, and means for displaying images corresponding to the image identification in the image display terminal that has received the image display instructions.

When an examination by CT or MRI is made, on the order of thousands (e.g., about 1500 to 2000) of slice images are generated for one examination. Accordingly, the image interpretation doctor must retrieve images at the same slice position as or a near slice position to the slice position of the image interpreted in the past examination from a vast amount of images. On this point, according to JP-P2002-342485A, the past image interpretation report and examination image on the same examination made for the same patient as the patient of this examination can be retrieved, however, only the image at the head of a series of slice images can be displayed. Therefore, the image interpretation doctor must view the images of one series sequentially from the head thereof for retrieving a desired slice image, which imposes a heavy burden on the doctor.

SUMMARY OF THE INVENTION

The present invention has been achieved in view of the above-mentioned problems. A purpose of the present invention is to provide an image interpretation report creating apparatus and an image interpretation support system capable of easily retrieving a key image corresponding to that used for image interpretation in the previous examination from among images taken in this examination to display the key image on an image display terminal (viewer).

In order to achieve the purpose, an image interpretation report creating apparatus according to one aspect of the present invention is to be connected to a server for storing report data representing image interpretation reports and at least one image display terminal for displaying examination images for diagnoses, and used for creating image interpretation report, and the apparatus includes: follow-up observation examination determining means for determining whether or not this examination is an object of follow-up observation; previous report determining means for determining, as previous report data, report data on the same patient as that of this examination from among the report data stored in the server in the case where this examination is an object of follow-up observation; previous report data acquiring means for acquiring the previous report data determined by the previous report determining means from the server; image data acquiring means for acquiring image data representing at least examination images at this time from image data storing means in which plural pieces of image data representing examination images are stored; key image estimating means for estimating a key image at a slice position corresponding to that of a key image used for image interpretation in the previous examination from among the examination images at this time based on the previous report data; and image data output means for outputting image data representing examination images containing the key image to the at least one image display terminal such that the key image is displayed in a predetermined format.

According to the image interpretation report creating apparatus of the present invention, the previous report as the most recent one of the image interpretation reports in the past on the same examination performed on the same patient as those in this examination is determined and the key image at the slice position corresponding to that of the key image used for image interpretation in the previous examination is estimated from among the examination images at this time based on the previous report data, and therefore, the key image corresponding to the previous key image can be easily retrieved and displayed on the image display terminal. Accordingly, the user's trouble of having to retrieve the key image can be avoided, and the time required for creating the image interpretation report can be reduced. As a result, the image interpretation report can be efficiently created.

BRIEF DESCRIPTION OF THE DRAWINGS

FIG. 1 is a block diagram showing a constitution of an image interpretation support system including an image interpretation report creating apparatus according to one embodiment of the present invention;

FIG. 2 is a schematic view showing examination images acquired by one examination;

FIG. 3 is a table (key image table) showing attendant information of a key image;

FIG. 4 is a block diagram showing the constitution of the image interpretation report creating apparatus as shown in FIG. 1;

FIG. 6 shows slice positions of key images in examination images at the previous time and this time;

DESCRIPTION OF THE PREFERRED EMBODIMENTS

Figure 5:
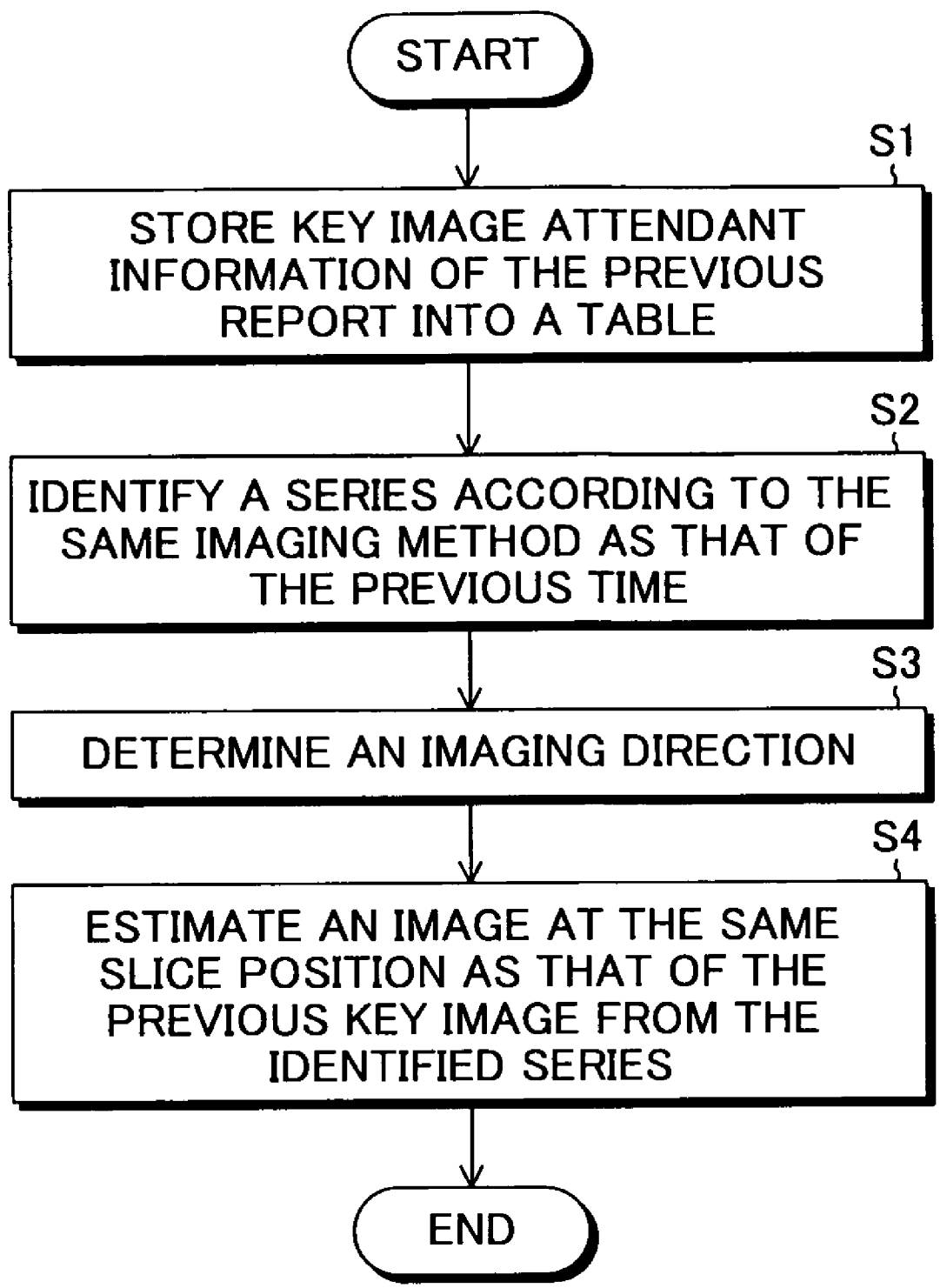
FIG. 5 is a flowchart showing a key image estimation method used in a key image estimating unit as shown in FIG. 4.

Hereinafter, preferred embodiments of the present invention will be explained in detail by referring to the drawings. The same reference numerals are assigned to the same component elements and the explanation thereof will be omitted.

FIG. 1 is a block diagram showing a constitution of an image interpretation support system including an image interpretation report creating apparatus according to one embodiment of the present invention.

The image interpretation support system includes an image interpretation report creating apparatus 1, at least one image display terminal (viewer) 2, an image server 3, and an image interpretation report server 4. Further, the image interpretation report creating apparatus 1 may be connected to an RIS (radiology information system) 5 and imaging modalities such as a CR apparatus 6a, a CT apparatus 6b, and an MRI apparatus 6c. As shown in FIG. 1, these apparatuses may be connected to one another via a network such as LAN (local area network).

As shown in FIG. 1, the image interpretation report creating apparatus 1 has a display unit 100 and an input unit 110. The display unit 100 is a display device for displaying a work list to be used by a user (image interpretation doctor) for selecting an examination for which image interpretation is to be performed, image interpretation reports during creation, and so on. Further, the input unit 110 is an input device such as a keyboard or mouse. FIG. 1 shows a state in which an image interpretation report 103 is displayed on a screen. The image interpretation report 103 contains an observation column 101, which shows text information inputted by the user, and a key image 102. The user creates an image interpretation report by entering text information and so on by using the input unit 110 into the image interpretation report 103 displayed on the display unit 100 while observing an examination image displayed on the image display terminal 2, which will be described later.

The image display terminal 2 is a terminal device for displaying an examination image as an object of image interpretation and has a high-definition display. FIG. 1 shows a state in which plural slice images are displayed in plural areas 210 on a screen 200, respectively. Although two image display terminals 2 are shown in FIG. 1, at least one image display terminal 2 is used at the time of image interpretation, and three or more image display terminals 2 may be used.

The image server 3 is, for example, a server for PACS (Picture Archiving and Communication System) for storing and managing image data acquired by the imaging modalities such as the CR apparatus 6a, CT apparatus 6b and MRI apparatus 6c. The image server 3 outputs desired image data to the image interpretation report creating apparatus 1 according to a request of the image interpretation report creating apparatus 1.

FIG. 2 is a schematic view showing examination images acquired by one examination. Typically, one or more series consisting of plural tomographic images at plural slice positions are acquired by performing CT examination or MRI examination. That is, sometimes plural imaging methods (imaging methods A, B, and C in FIG. 2) are used in an examination, and plural series of images (series 1, 2, and 3 in FIG. 2) are acquired according to those imaging methods. For example, in CT examination, a plane CT imaging method and a contrast CT imaging method are performed, and in MRI examination, a T1 enhancement image imaging method, a T2 enhancement image imaging method and an SE (spin echo) imaging method are performed. In the embodiment, the image data is managed with image attendant information including examination ID, examination date, patient ID, series numbers and examination parts according to standards of DICOM (digital imaging and communication medicine).

Referring to FIG. 1 again, the image interpretation report server 4 stores report data representing image interpretation reports created in the past. The report data includes report ID, patient ID, name of patient, information for identifying examination as an object of image interpretation, text information shown as observations by image interpretation doctors, key image data, image attendant information thereof, annotation information. Here, a key image is an image determined by an image interpretation doctor as a key of image interpretation from among a series of images obtained by one examination, and at least one image is set as a key image for one examination.

As the key image, a slice image intelligibly showing a lesion part, a slice image showing a part that is especially noteworthy, or a slice image determined as being suitable for image interpretation is selected. The slice image as a key image is converted into a general-purpose image format such as a JPEG format and bitmap format, and displayed as attached onto the image interpretation report 103. Further, the annotation information includes observations entered by doctors while examination images are consulted, and signs such as arrows and lines surrounding areas displayed on the key image for indicating parts to be carefully observed.

FIG. 3 is a table (key image table) showing attendant information of a key image in an interpretation report. The key image table is stored in a recording medium such as a hard disk in the image interpretation report creating apparatus 1. In FIG. 3, two key images (key image ID: "0011", "0012") are set for the image interpretation report identified by a report ID of "00001".

The attendant information of each key image includes (i) information for identifying a type of series including a series number of DICOM, a protocol name, series description, an examination part and so on, and (ii) information for identifying a slice position of the key image including a patient position, an image position, an image number ("K" shown in FIG. 2), a slice thickness ("$\Delta t$" shown in FIG. 2) and a slice position ("L" shown in FIG. 2). Further, for MR images acquired by the MRI apparatus, information such as an image type, scanning sequence, sequence modification and scan options is also used according to the imaging method.

The image interpretation report server 4 outputs desired report data to the image interpretation report creating apparatus 1 according to a request of the image interpretation report creating apparatus 1.

The RIS 5 is a server for managing radiological examinations in the radiological department, and manages examination schedules, sends examination orders to the imaging modalities, and sends image interpretation orders for examinations, for which imaging has been finished, based on information such as the patient information and details of examination inputted by using the input terminal.

Next, a constitution of the image interpretation report creating apparatus as shown in FIG. 1 according to the embodiment will be explained by referring to FIGS. 1 and 4.

FIG. 4 is a block diagram showing the constitution of the image interpretation report creating apparatus as shown in FIG. 1. As shown in FIG. 4, the image interpretation report creating apparatus 1 includes, in addition to the display unit 100 and input unit 110 that have been described above, a central processing unit (hereinafter, referred to as CPU) 10, a memory 120 for temporarily storing report data received from the image interpretation report server 4, image data received from the image server 3 and so on, a hard disk control unit 130 for controlling a hard disk 131 as a recording medium, and a network interface 140. These are connected via a bus line to one another. Further, the CPU 10 is connected to a network via the network interface 140.

In the hard disk 131, in addition to the key image table, software (program) for actuating the CPU 10 to perform processing is recorded. As the recording medium, not only the built-in hard disk 131 but also an external hard disk, a flexible disk, an MO, an MT, a RAM, a CD-ROM, a DVD-ROM and so on may be used.

Next, plural function blocks formed of the CPU 10 and software (program) will be explained. These function blocks includes a follow-up observation examination determining unit 11, a previous report determining unit 12, a previous report data acquiring unit 13, a key image estimating unit 14, a key image determining unit 15, an image data acquiring unit 16, an image data output unit 17, a draft generating unit 18, a report creating unit 19, a text comparing unit 20, a report saving unit 21 and a work list creating unit 22.

The follow-up observation examination determining unit 11 determines whether or not an examination, on which an image interpretation report is to be created, is an examination as an object of follow-up observation. For example, in the case where it is found that the same kind of examination is performed within a predetermined period (e.g., within six months) on the same part of the same patient as a result of referring to the work list in the past, the examination is determined as being an object of follow-up observation. The period, within which an examination is determined as an object of follow-up observation, may be designated by the user settings. Alternatively, in the case where an examination is clearly stated as an object of follow-up observation in the details of the request of examination, or in the case where order information of an examination contains information representing that the examination is an object of follow-up observation, the examination is also determined as being an object of follow-up observation.

Such judgment may be performed at the time when the user selects an examination from the work list when performing image interpretation, or at the time when new image data is stored in the image server, or at the time when image interpretation is ordered from the RIS.

When an examination, on which an image interpretation report is to be created, is determined as being an examination as an object of follow-up observation, the previous report determining unit 12 determines the most recent image interpretation report on the same kind of examination performed on the same part of the same patient as those of the examination at this time from among the image interpretation reports in the past represented by report data stored in the image interpretation report server 4. As below, the image interpretation report determined by the previous report determining unit 12 is referred to as "previous report".

The previous report acquiring unit 13 reads out the report data representing the previous report from the image interpretation report server 4, thereby acquiring the report. Further, the previous report data acquiring unit 13 outputs attendant information of the key image from the acquired report data to the key image estimating unit 14, and outputs text information to be displayed as observations and annotation information to the draft generating unit 18.

The image data acquiring unit 16 acquires examination image data at this time and examination image data at the previous time from the image server 3. Further, the image data acquiring unit 16 outputs image data for displaying examination image on the image display terminal 2 to the image data output unit 17, and converts image data at the slice position to be used as the key image into a general-purpose image format such as JPEG format or bitmap format and outputs it as key image data to the draft generating unit 18. Although the image interpretation report creating apparatus 1 acquires image data from the image server 3 online in the embodiment, the apparatus may acquire the image data offline from recording media such as DVD (digital versatile disk) and CD (compact disk).

The key image estimating unit 14 estimates a key image in this examination based on the attendant information of the key image in the previous examination. Here, a key image estimation method used in the key image estimating unit 14 will be explained by referring to FIGS. 3 to 6.

FIG. 5 is a flowchart showing the key image estimation method by the key image estimating unit as shown in FIG. 4. At step S1 in FIG. 5, the key image estimating unit 14 stores the attendant information of the key image outputted from the previous report data acquiring unit 13 into the key image table.

Then, at step S2, the key image estimating unit 14 identifies a series, which corresponds to the series containing the key image in the previous examination, in the examination images at this time based on items for identifying the type of series such as the series number, protocol name, series description and examination part included in the attendant information of the key image in the previous report data stored in the key image table. The series matching in at least one or desirably all of these items is estimated to represent the same part imaged in the same kind of examination and according to the same imaging method as those in the previous examination. In the case of MRI examination, in addition to the above items, items such as an image type, scanning sequence, sequence modification and scan options are also used.

As shown in FIG. 6, in the previous examination images, the K-th slice image of the series 2 is the key image. Accordingly, at step S2, the key image estimating unit 14 identifies the series (series 2 of the examination images at this time), which is obtained by using the imaging method B in consistent with the imaging method of the previous series 2, in the examination images at this time.

Then, at step S3, the key image estimating unit 14 determines whether or not the imaging direction of this series identified at step S2 is the same as that at the previous time based on the patient position contained in the information for identifying the slice position of the key image. Here, the imaging direction represents that from which of the head part or leg part of the patient and in which direction imaging has been performed. In the case where the imaging direction at this time is different from that at the previous time as a result of judgment, the image numbers are counted in the reverse sequence when the key image at this time is identified.

Then, at step S4, the key image estimating unit 14 estimates, as the key image at this time, the image at the same slice position as that of the previous key image from the series identified at step S2 based on the information for identifying the slice position of the previous key image (see FIG. 3). Here, when the slice thickness is common between the previous series and this series, the slice image as the key image at this time can be obtained based on the image number, image position or slice position.

However, when the slice thickness is not common, the slice image at this time is estimated in the following manner by using the slice thickness and image number in each series. That is, as shown in FIG. 6, assuming that the image number of the previous key image is K when the slice thickness in the previous series is $\Delta t_1$ and the slice thickness in this series is $\Delta t_2$, the K'-th slice image that satisfies $\Delta t_1 \times K = \Delta \Delta t_2 \times K'$ is estimated as the key image at this time. Alternatively, the K'-th slice image that minimizes the absolute value of the difference between $\Delta t_1 \times K$ and $\Delta t_2 \times K'$ is estimated as the key image at this time. Thus, the key image in the position nearest the position of the previous slice image is estimated as the key image at this time.

Referring FIG. 4 again, the key image determining unit 15 determines the slice image estimated by the key image estimating unit 14 as the key image in this examination. Alternatively, the user may designate the slice image different from the estimated key image as the key image by viewing the images displayed on the image display terminal 2 (FIG. 1) and adjusting the slice position of the slice image to be set as the key image. In this case, the key image determining unit 15 determines the slice image designated by the user as the key image.

The image data output unit 17 outputs the image data representing the examination images at this time or both the image data representing the examination images at this time and the image data representing the examination images at the previous time to the image display terminal 2. In this regard, the image data output unit 17 sets the display format such that the plural slice images are located in the plural areas on the screen, respectively, with reference to the estimated or determined key image. Whether only the examination images at this time or both of the examination images at this time and the previous time are displayed may be set in advance, or may be automatically set according to the number of the image display terminals 2 connected to the image interpretation report creating apparatus 1, or the desired format may be selected by the user.

Here, the display format of examination image will be explained by referring to FIGS. 7 to 9B.

Figure 7:
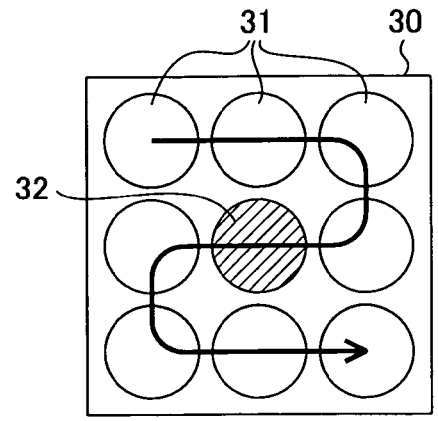
FIG. 7 shows a display format of examination images when one image display terminal is used.

FIG. 7 shows a display format when one image display terminal is used at the time of image interpretation. In this case, plural slice images contained in one series are located in plural areas 31 on a screen 30 in the order of image number as shown by the arrow in FIG. 7. In this regard, the image numbers are adjusted such that the key image is located in an area 32 positioned nearly at the center of the screen 30.

Figure 8A:
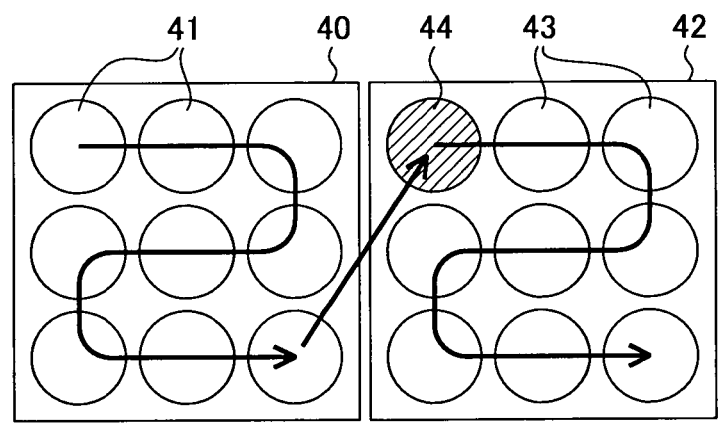
FIGS. 8A and 8B show display formats of examination images when two image display terminals are used.
Figure 8B:
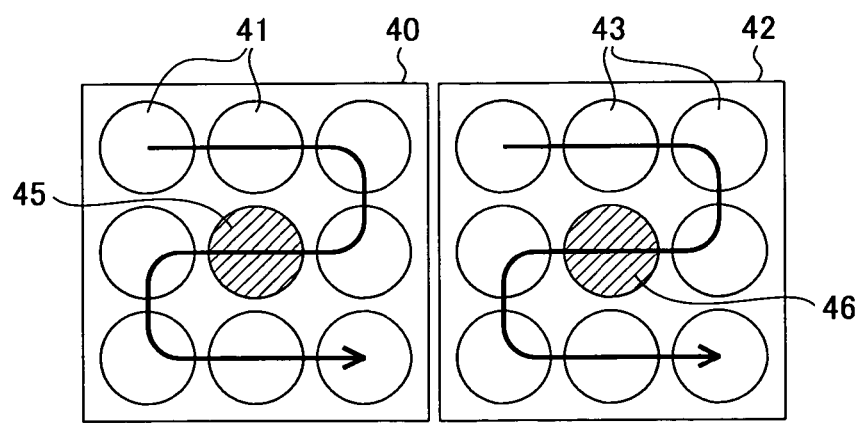

FIGS. 8A and 8B show display formats when two image display terminals are used at the time of image interpretation. As shown in FIG. 8A, when only the examination images at this time are displayed on the screens, plural slice images contained in one series are located in areas 41 on a screen 40 and areas 43 on a screen 42 in the order of image number as shown by the arrows in the drawing. In this regard, the image numbers are adjusted such that the key image is located in an area 44 on the upper left of the screen 42 and positioned nearly at the center of all of the areas 41 and 43.

On the other hand, as shown in FIG. 8B, when both of the examination images at this time and the previous time are displayed on the screens, the examination images at this time are located in the areas 41 on the screen 40 and the examination images at the previous time are located in the areas 43 on the screen 42. In this regard, the image numbers are adjusted such that the estimated key image at this time and the previous key image are located in areas 45 and 46 positioned nearly at the centers of screens 40 and 42, respectively. In this case, the user easily fine-adjusts the slice position of the key image in this examination by referring to the examination images at the previous time.

Figure 9A:
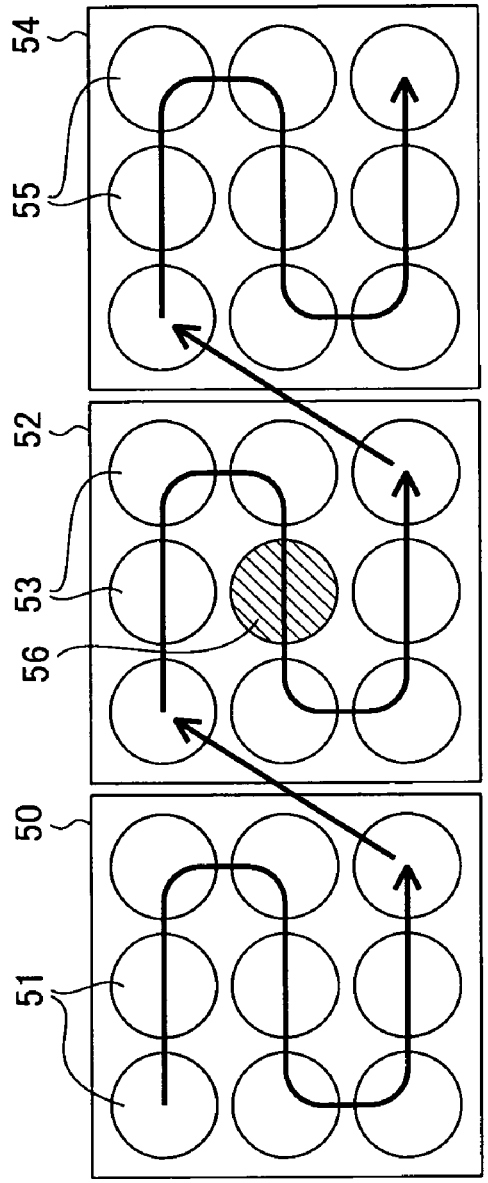
FIGS. 9A and 9B show display formats of examination images when three image display terminals are used.
Figure 9B:
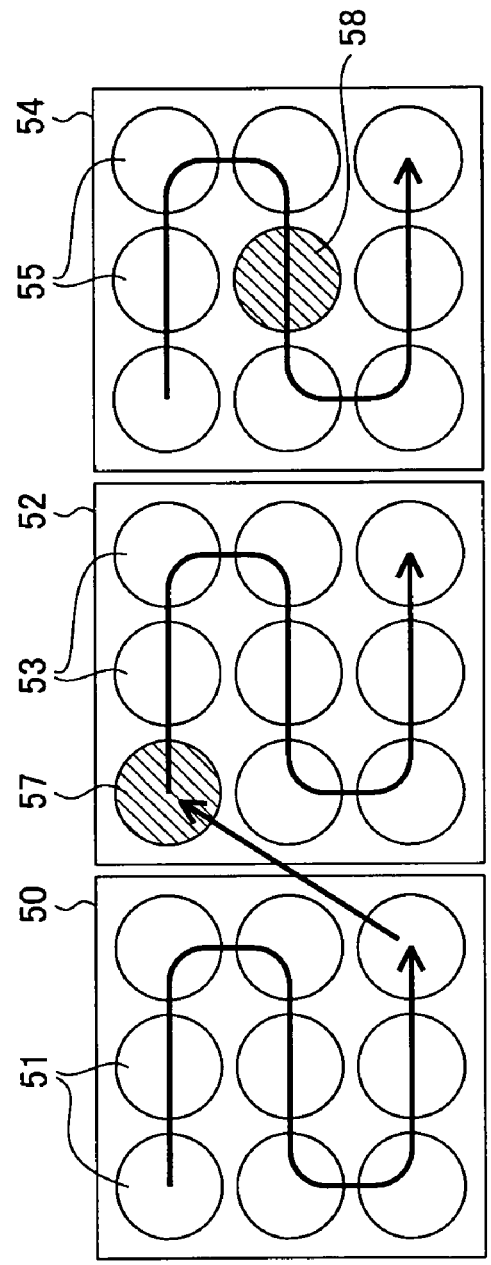

FIGS. 9A and 9B show display formats when three image display terminals are used at the time of image interpretation. As shown in FIG. 9A, when only the examination images at this time are displayed on the screen, plural slice images are located in areas 51 on a screen 50, areas 53 on a screen 52, and areas 55 on a screen 54 in the order of image number as shown by the arrows in the drawing. In this regard, the image numbers are adjusted such that the estimated key image is located in an area 56 at the center of the screen 52 and positioned nearly at the center of all of the areas 51, 53 and 55.

As shown in FIG. 9B, when both of the examination images at this time and the previous time are displayed on the screens, plural slice images in this examination are located in the areas 51 on the screen 50 and the areas 53 on the screen 52 in the order of image number as shown by the arrows in FIG. 9B. In this regard, the image numbers are adjusted such that the estimated key image at this time is located in an area 57 on the upper left of the screen 52 positioned nearly at the center of areas 51 and 53. On the other hand, plural slice images in the previous examination are located in the area 55 on the screen 44 in the order of image number such that the previous key image is positioned in a center area 58 of the screen 54. In this case, the user can easily fine-adjust the slice position of the key image in this examination by referring to the examination images at the previous time.

The draft generating unit 18 creates a draft of image interpretation report based on the text information and the annotation information outputted from the previous report acquiring unit 13, and the key image data outputted from the image data acquiring unit 16.

Figure 10:
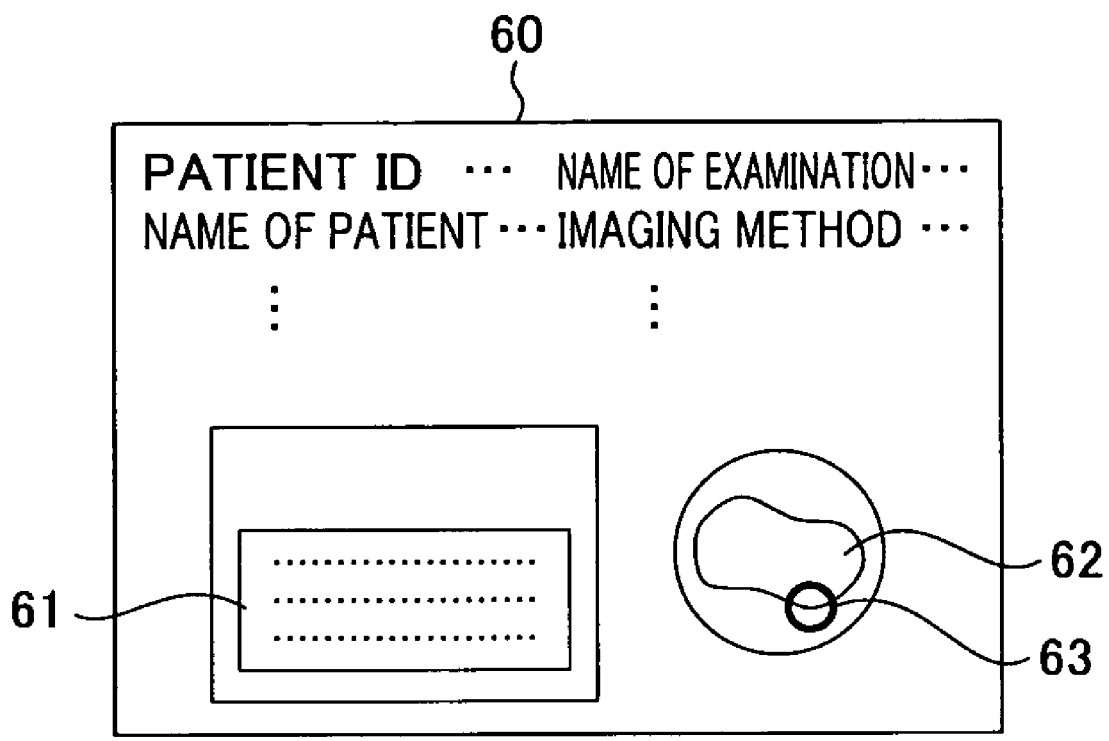
FIG. 10 is a schematic view showing a draft of image interpretation report generated by a draft generating unit as shown in FIG. 4.

FIG. 10 is a schematic view showing a draft of image interpretation report generated by the draft generating unit as shown in FIG. 4. In an image interpretation report 60, information on a patient as an object of examination (patient ID, name of patient and so on) and information on the examination (name of examination, imaging method and so on) are displayed. In an observation column 61, the same observation (text information) as that in the previous report is displayed.

Further, in a key image column 62, the key image in this examination is attached based on the key image data outputted from the image data acquiring unit 16. Furthermore, annotation information 63 in the previous report is attached and displayed on the key image at this time.

Referring to FIG. 4 again, the report creating unit 19 generates report data representing this image interpretation report by rewriting the observation column 61 (see FIG. 10) in the draft based on the text information inputted by the user using the input unit 110. Further, when the user changes the position of the annotation information or adds annotation information, the report creating unit 19 rewrites and adds the annotation information. Further, the report creating unit 19 displays the image interpretation report on the screen of the display unit 100 based on the data representing the draft of the interpretation report or the data representing the image interpretation report during creation by the user.

When a save request of image interpretation report is made, the text comparing unit 20 compares the text information in the image interpretation report currently displayed on the display screen of the display unit 100 with the text information in the draft of image interpretation report. Then, in the case where there is a difference between them, the image interpretation report is determined as having been edited. Contrary, in the case where there is no difference between them, the image interpretation report is determined as not yet having been edited.

In the case where the image interpretation report is determined as having been edited by the text comparing unit 20, the report saving unit 21 saves the image interpretation report currently displayed on the display screen of the display unit 100 as a report at this time in the hard disk 131 or the like, and transmits the report to the image interpretation report server 4 and allows the server to store it. In this regard, the information on the slice image used as the key image is saved as attendant information of the key image (see FIG. 3) together with the key image data in this examination. On the other hand, in the case where the image interpretation report is determined as not yet having been edited by the text comparing unit 20, the report saving unit 21 does not save the report.

The work list creating unit 22 creates a work list for follow-up observation by extracting the examinations determined as being objects of follow-up observation by the follow-up observation examination determining unit 11. The work list creating unit 22 may display the examinations in order of descending frequency of performed examinations in the past in the work list. Thus classifying examinations improves the efficiency of image interpretation work. Further, in the case where the examination is frequent, report data representing image interpretation reports in the past have been stored, the image interpretation and entrance of observations become relatively easier. Therefore, assigning such an examination to an image interpretation doctor at a relatively low level of skill such as an intern doctor enables the entire image interpretation work to be efficiently carried out and helps the image interpretation doctor to improve his or her own image interpretation technique.

Figure 11:
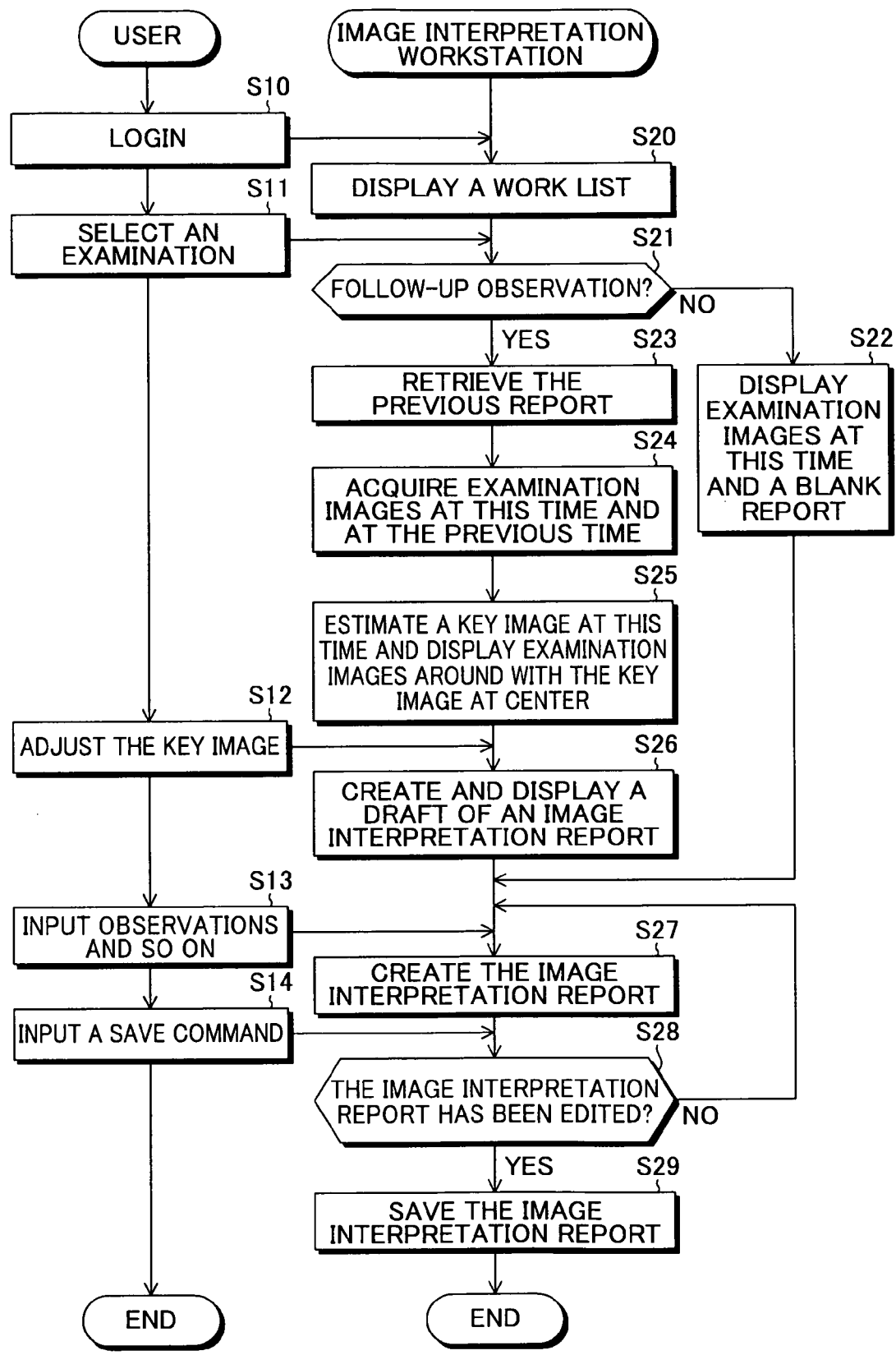
FIG. 11 is a flowchart showing an operation of the image interpretation report creating apparatus as shown in FIG. 1.

Next, an image interpretation report creation operation by the image interpretation report creating apparatus according to the embodiment will be explained by referring to FIG. 11. FIG. 11 is a flowchart showing an operation of the image interpretation report creating apparatus as shown in FIG. 1.

When a user logs into the image interpretation report creating apparatus 1 at step S10 in FIG. 11, the image interpretation report creating apparatus 1 starts operation in response thereto and displays a work list on the display unit 100 at step S20. Alternatively, the image interpretation report creating apparatus 1 may start operation when new image data is stored in the image server 3, or when image interpretation on an examination is ordered from the RIS 5.

When the user selects an examination waiting for image interpretation from the work list at step S11, the image interpretation report creating apparatus 1 determines whether or not the selected examination is an object of follow-up observation at step S21. In the case where the image interpretation report creating apparatus 1 displays a work list for follow-up observation and the user selects an examination from the list, the judgment at step S21 may be omitted.

If the examination is determined as not being an object of follow-up observation at step S21, the image interpretation report creating apparatus 1 displays examination images from the head of the series on the image display terminal 2 and displays an image interpretation report with a blank observation column 101 on the display unit 100 at step S22. In this case, the user may select any slice image, thereby the slice image is attached to the image interpretation report as the key image.

On the other hand, if the examination is determined as being an object of follow-up observation at step S21, the image interpretation report creating apparatus 1 retrieves report data representing the previous report and acquires it from the report data stored in the image interpretation report server 4 at step S23. Further, the image interpretation report creating apparatus 1 acquires image data representing the examination images at this time and image data representing the examination images at the previous time from the image data stored in the image server 3 at step S24.

Then, at step S25, the image interpretation report creating apparatus 1 estimates the key image at this time based on the previous report as has been described by referring to FIG. 5, and further, as shown in FIG. 8B, configures display settings with reference to the key image and allows the two image display terminals to display the examination images at this time and the examination images at the previous time. Thus estimating and displaying the key image in this examination enable the user to avoid the trouble of having to retrieve the slice image at this time corresponding to the key image in the previous examination, and therefore, the time required for image interpretation can be reduced. As a result, the image interpretation efficiency can be improved.

The user may adjust the slice position of the key image before and after, while viewing the examination images at this time displayed on the image display terminal 2 at step S12. In this case, the image interpretation report creating apparatus 1 determines the slice image selected by the user as the key image, and redisplays the examination images at this time.

At step S26, the image interpretation report creating apparatus 1 creates a draft of image interpretation report based on the text information and the annotation information of the previous report and the key image estimated or determined at this time, and displays it on the display unit 100. Thus, automatically creating a draft can reduce the time required for report creation by the user.

At step S13, the user observes the examination images at this time displayed on the image display terminal 2, and enters observations by using the input unit 110. In response thereto, the image interpretation report creating apparatus 1 rewrites the observation column 101 and creates an image interpretation report (step S27). Further, the user may change or add the annotation information according to need. Thus, employing the input format of rewriting the draft makes the entrance of observations easier for the user, and reduces the time required for report creation. Further, referring to the previous observations helps even an intern doctor at a low level of skill to enter observations.

When the entrance of observations is finished, the user inputs a save command of image interpretation report at step S14. In response thereto, the image interpretation report creating apparatus 1 determines whether or not the image interpretation report have been edited by comparing text information in the current image interpretation report with the text information in the draft (step S28).

If the image interpretation report is determined as not yet having been edited, the image interpretation report creating apparatus 1 does not save the image interpretation report and returns to the creation operation of image interpretation report. On the other hand, if the image interpretation report is determined as having been edited, the image interpretation report creating apparatus 1 saves the edited report as the image interpretation report at this time and transmits the report data representing the edited report to the image interpretation report server 4 and allows the server to store it at step S29. Thus, comparing the current image interpretation report with the draft thereof before saving the image interpretation report can prevent the in edited report from being saved as the current image interpretation report by mistake.

The invention claimed is:

1. An image interpretation report creating apparatus to be connected to a server for storing report data representing image interpretation reports and at least one image display terminal for displaying examination images for diagnoses, and used for creating an image interpretation report, said apparatus comprising:
   follow-up observation examination determining means for determining whether or not this examination is an object of follow-up observation;
   previous report determining means for determining, as previous report data, report data related to a previous examination which is the same examination performed on the same patient as those in this examination from among the report data stored in said server in the case where said follow-up observation examination determining means determines that this examination is an object of follow-up observation;
   previous report data acquiring means for acquiring the previous report data determined by said previous report determining means from said server, said previous report data including attendant information of a previous key image used for image interpretation in the previous examination;
   image data acquiring means for acquiring image data representing at least examination images at this time from image data storing means in which plural pieces of image data representing examination images are stored;
   key image estimating means for estimating, as a key image in this examination, an image at a slice position corresponding to that of the previous key image from among the examination images at this time based on a slice thickness and at least one of an image number, an image position, and a slice position included in the attendant information of the previous key image; and
   image data output means for outputting image data representing examination images including the key image to said at least one image display terminal such that the key image is displayed in a predetermined format.

2. An image interpretation report creating apparatus according to claim 1, wherein said previous report determining means determines, as the previous report data, report data representing the most recent one of the image interpretation reports in the past on the same examination performed on the same patient as those in this examination.

3. An image interpretation report creating apparatus to be connected to a server for storing report data representing image interpretation reports and at least one image display terminal for displaying examination images for diagnoses, and used for creating an image interpretation report, said apparatus comprising:
   follow-up observation examination determining means for determining whether or not this examination is an object of follow-up observation;
   previous report determining means for determining, as previous report data, report data related to a previous examination which is the same examination performed on the same patient as those in this examination from among the report data stored in said server in the case where said follow-up observation examination determining means determines that this examination is an object of follow-up observation;
   previous report data acquiring means for acquiring the previous report data determined by said previous report determining means from said server, said previous report data including attendant information of a previous key image used for image interpretation in the previous examination;
   image data acquiring means for acquiring image data representing at least examination images at this time from image data storing means in which plural pieces of image data representing examination images are stored;
   key image estimating means for estimating, as a key image in this examination, an image from among the examination images at this time based on the attendant information of the previous key image, said image having an image number of K' that minimizes an absolute value of a difference between $\Delta t_1 \times K$ and $\Delta t_2 \times K'$ where an image number of the previous key image is K, a slice thickness in a previous series is $\Delta t_1$, and a slice thickness in this series is $\Delta t_2$; and
   image data output means for outputting image data representing examination images including the key image to said at least one image display terminal such that the key image is displayed in a predetermined format.

4. An image interpretation report creating apparatus according to claim 1, wherein said key image estimating means estimates, as the key image in this examination, an image at a slice position nearest to that of the previous key image in this series in the case where this series has the same slice thickness as that of a previous series.

5. An image interpretation report creating apparatus according to claim 1, wherein said image data output means outputs the image data while setting a display format of examination images such that the key image estimated by said key image estimating means is located in an area having a predetermined position.

6. An image interpretation report creating apparatus according to claim 1, further comprising:
   key image determining means for determining an image to be set as the key image from among the examination images at this time based on information inputted by a user.

7. An image interpretation report creating apparatus according to claim 1, further comprising:
   draft generating means for generating a draft of the image interpretation report based on the previous report data acquired by said previous report data acquiring means and the key image in this examination.

8. An image interpretation report creating apparatus according to claim 7, further comprising:
  comparing means for comparing, when the user issues a save command of the image interpretation report, text information in the image interpretation report currently displayed on a display screen of display means with text information in the draft of the image interpretation report generated by said draft generating means to determine whether or not there is a difference therebetween; and
  saving means for saving the image interpretation report currently displayed on the display screen of said display means as an image interpretation report at this time in the case where said comparing means determines that there is a difference.

9. An image interpretation support system comprising:
  image data storage means for storing image data representing at least examination images in previous examinations;
  image interpretation report storage means for storing at least report data representing image interpretation reports in the previous examinations;
  follow-up observation examination determining means for referring to examination information to determine that this examination is an object of follow-up observation in the case where the same examination was performed on the same patient within a predetermined period;
  previous report determining means for determining, as previous report data, report data related to a previous examination which is the same examination performed on the same patient as those in this examination from among the report data stored in said image interpretation report storage means in the case where said follow-up observation examination determining means determines that this examination is an object of follow-up observation;
  previous report data acquiring means for acquiring the previous report data determined by said previous report determining means from said image interpretation report storage means, said previous report data including attendant information of a previous key image used for image interpretation in the previous examination; and
  image data acquiring means for acquiring, from said image data storage means, image data representing the previous key image from among the examination images in the previous examination based on the attendant information of the previous key image.

10. An image interpretation support system according to claim 9, wherein said previous report determining means determines, as the previous report data, report data representing the most recent one of the image interpretation reports in the past on the same examination performed on the same patient as those in this examination.

11. An image interpretation support system according to claim 9, further comprising:
  key image estimating means for estimating, as a key image in this examination, an image at a slice position corresponding to that of the previous key image from among examination images at this time based on a slice thickness and at least one of an image number, an image position, and a slice position included in the attendant information of the previous key image.

12. An image interpretation support system comprising:
  image data storage means for storing image data representing at least examination images in previous examinations;
  image interpretation report storage means for storing at least report data representing image interpretation reports in the previous examinations;
  follow-up observation examination determining means for referring to examination information to determine that this examination is an object of follow-up observation in the case where the same examination was performed on the same patient within a predetermined period;
  previous report determining means for determining, as previous report data, report data related to a previous examination which is the same examination performed on the same patient as those in this examination from among the report data stored in said image interpretation report storage means in the case where said follow-up observation examination determining means determines that this examination is an object of follow-up observation;
  previous report data acquiring means for acquiring the previous report data determined by said previous report determining means from said image interpretation report storage means, said previous report data including attendant information of a previous key image used for image interpretation in the previous examination;
  image data acquiring means for acquiring, from said image data storage means, image data representing the previous key image from among the examination images in the previous examination based on the attendant information of the previous key image; and
  key image estimating means for estimating, as a key image in this examination, an image from among the examination images at this time based on the attendant information of the previous key image included in the previous report data, said image having an image number of K' that minimizes an absolute value of a difference between $\Delta t_1 \times K$ and $\Delta t_2 \Delta K'$ where an image number of the previous key image is K, a slice thickness in a previous series is $\Delta t_1$, and a slice thickness in this series is $\Delta t_2$.

13. An image interpretation support system according to claim 11, wherein said key image estimating means estimates, as the key image in this examination, an image at a slice position nearest to that of the previous key image in this series in the case where this series has the same slice thickness as that of a previous series.

14. An image interpretation support system according to claim 9, wherein said image data acquiring means acquires, from said image data storage means, image data representing the previous key image from among examination images in a previous examination which is the same examination performed on the same part of the same patient as those in this examination.

15. An image interpretation support system according to claim 14, wherein said image data acquiring means acquires, from said image data storage means, image data representing the previous key image from among examination images in a previous examination which is the same examination performed on the same part of the same patient in a predetermined period as those in this examination.

16. An image interpretation support system according to claim 11, further comprising:
  image data output means for outputting image data to an image display terminal such that the key image in this examination is displayed in a predetermined format in said image display terminal.

17. An image interpretation support system according to claim 11, further comprising:
  key image determining means for determining an image to be set as the key image from among examination images at this time based on information inputted by a user.

18. An image interpretation support system according to claim 9, further comprising:
   draft generating means for generating a draft of the image interpretation report based on the previous report data acquired by said previous report data acquiring means and the key image in this examination.

19. An image interpretation support system according to claim 18, further comprising:
   comparing means for comparing, when the user issues a save command of the image interpretation report, text information inputted or updated by the user with text information in the draft of the image interpretation report generated by said draft generating means to determine whether or not there is a difference therebetween; and
   saving means for saving the image interpretation report including text information inputted or updated by the user as an image interpretation report at this time into said image interpretation report storage means in the case where said comparing means determines that there is a difference.

* * * * *